US011618805B2

(12) United States Patent
Nam et al.

(10) Patent No.: US 11,618,805 B2
(45) Date of Patent: Apr. 4, 2023

(54) METHOD FOR PREPARING SUPERABSORBENT POLYMER, AND SUPERABSORBENT POLYMER PREPARED THEREBY

(71) Applicant: LG Chem, Ltd., Seoul (KR)

(72) Inventors: Hye Mi Nam, Daejeon (KR); Min Ho Hwang, Daejeon (KR); Sang Gi Lee, Daejeon (KR); Tae Hwan Jang, Daejeon (KR); Soo Jin Lee, Daejeon (KR)

(73) Assignee: LG Chem, Ltd.

( * ) Notice: Subject to any disclaimer, the term of this patent is extended or adjusted under 35 U.S.C. 154(b) by 126 days.

(21) Appl. No.: 16/871,301

(22) Filed: May 11, 2020

(65) Prior Publication Data

US 2020/0270403 A1 Aug. 27, 2020

Related U.S. Application Data

(62) Division of application No. 15/556,083, filed as application No. PCT/KR2016/003946 on Apr. 15, 2016, now Pat. No. 10,696,800.

(30) Foreign Application Priority Data

Jul. 6, 2015 (KR) .................. 10-2015-0095926

(51) Int. Cl.
*C08J 3/075* (2006.01)
*C08J 3/24* (2006.01)
*C08F 220/10* (2006.01)
*C08K 5/00* (2006.01)
*A61L 15/60* (2006.01)
*C08L 33/06* (2006.01)
*C08G 65/34* (2006.01)
*C08L 1/02* (2006.01)

(52) U.S. Cl.
CPC .............. *C08J 3/075* (2013.01); *A61L 15/60* (2013.01); *C08F 220/10* (2013.01); *C08J 3/24* (2013.01); *C08K 5/00* (2013.01); *C08L 33/06* (2013.01); *C08G 65/34* (2013.01); *C08J 2333/02* (2013.01); *C08L 1/02* (2013.01)

(58) Field of Classification Search
CPC .......... C08J 3/075; C08J 3/24; C08J 2333/02; A61L 15/60; C08F 220/10; C08L 33/06; C08L 1/02; C08L 2333/02; C08G 65/34; C08K 5/00
USPC ........................................................ 524/35
See application file for complete search history.

(56) References Cited

U.S. PATENT DOCUMENTS

| | | | |
|---|---|---|---|
| 4,883,478 A | 11/1989 | Lerailler et al. |
| 4,973,632 A | 11/1990 | Nagasuna et al. |
| 5,032,628 A | 7/1991 | Choi et al. |
| 5,118,719 A | 6/1992 | Lind |
| 5,328,935 A | 7/1994 | Van Phan et al. |
| 5,563,218 A | 10/1996 | Rebre et al. |
| 5,712,316 A | 1/1998 | Dahmen et al. |
| 5,985,944 A | 11/1999 | Ishizaki et al. |
| 6,107,358 A | 8/2000 | Harada et al. |
| 6,133,193 A | 10/2000 | Kajikawa et al. |
| 6,174,929 B1 | 1/2001 | Hahnle et al. |
| 6,414,214 B1 | 7/2002 | Engelhardt et al. |
| 6,565,768 B1 | 5/2003 | Dentler et al. |
| 6,750,262 B1 | 6/2004 | Hahnle et al. |
| 7,638,570 B2 | 12/2009 | Torii et al. |
| 7,803,880 B2 | 9/2010 | Torii et al. |
| 2001/0038831 A1 | 11/2001 | Park et al. |
| 2004/0019342 A1 | 1/2004 | Nagasuna et al. |
| 2004/0214946 A1 | 10/2004 | Smith et al. |
| 2005/0054784 A1 | 3/2005 | Qin et al. |
| 2005/0137546 A1 | 6/2005 | Joy et al. |
| 2005/0256469 A1 | 11/2005 | Qin et al. |
| 2006/0204755 A1 | 9/2006 | Torii et al. |
| 2007/0066167 A1 | 3/2007 | Wada et al. |
| 2007/0123658 A1 | 5/2007 | Torii et al. |
| 2007/0141338 A1 | 6/2007 | Ishizaki et al. |
| 2008/0058747 A1 | 3/2008 | Singh Kainth et al. |
| 2008/0139693 A1 | 6/2008 | Ikeuchi et al. |
| 2008/0161499 A1 | 7/2008 | Riegel et al. |
| 2008/0215026 A1 | 9/2008 | Schornick et al. |
| 2008/0234645 A1 | 9/2008 | Dodge et al. |
| 2009/0196848 A1 | 8/2009 | Davis |
| 2010/0057027 A1 | 3/2010 | Furno et al. |
| 2010/0099781 A1 | 4/2010 | Tian et al. |
| 2011/0204288 A1 | 8/2011 | Funk et al. |
| 2011/0313113 A1 | 12/2011 | Sakamoto et al. |

(Continued)

FOREIGN PATENT DOCUMENTS

CN 1856331 A 11/2006
CN 101094696 A 12/2007

(Continued)

OTHER PUBLICATIONS

Riehm et al., Langmuir, (2016), v32, p. 3954-3962.
Buchholz, et al., Modern Superabsorbent Polymer Technology, 1998, vol. 152, pp. 199-201, New York: Wiley-vch.
Extended European Search Report including Written Opinion for Application No. EP16803731.5 dated Sep. 3, 2018.
Extended European Search Report including Written Opinion for Application No. EP16811803.2 dated Aug. 27, 2018.
Extended European Search Report including Written Opinion for Application No. EP16835267.2 dated Aug. 22, 2018.

(Continued)

*Primary Examiner* — Frances Tischler
(74) *Attorney, Agent, or Firm* — Lerner, David, Littenberg, Krumholz & Mentlik, LLP

(57) ABSTRACT

The present invention relates to a method for preparing a superabsorbent polymer, and a superabsorbent polymer prepared thereby. A superabsorbent polymer prepared by the preparation method exhibits minimized deterioration of physical properties after being pulverized, and thus basic absorbance performance is excellent and an excellent liquid permeability and absorbance rate can be exhibited.

6 Claims, 3 Drawing Sheets

(56) References Cited

U.S. PATENT DOCUMENTS

| | | |
|---|---|---|
| 2012/0045639 A1 | 2/2012 | Whitmore et al. |
| 2012/0184670 A1 | 7/2012 | Kobayashi et al. |
| 2012/0184684 A1 | 7/2012 | Funk et al. |
| 2012/0219728 A1 | 8/2012 | Badri et al. |
| 2012/0232177 A1 | 9/2012 | Lopez Villanueva et al. |
| 2012/0258851 A1 | 10/2012 | Nakatsuru et al. |
| 2012/0296296 A1 | 11/2012 | Di Cintio et al. |
| 2012/0296297 A1 | 11/2012 | Di Cintio et al. |
| 2012/0296298 A1 | 11/2012 | Gray et al. |
| 2012/0296299 A1 | 11/2012 | Villanueva et al. |
| 2012/0309619 A1 | 12/2012 | Kwon et al. |
| 2013/0102750 A1 | 4/2013 | Watanabe et al. |
| 2013/0172180 A1 | 7/2013 | Naumann et al. |
| 2014/0066584 A1 | 3/2014 | Peterson et al. |
| 2014/0127510 A1 | 5/2014 | Handa et al. |
| 2014/0296423 A1 | 10/2014 | Ebata et al. |
| 2014/0306155 A1 | 10/2014 | Tian et al. |
| 2014/0306156 A1 | 10/2014 | Tian et al. |
| 2014/0312273 A1 | 10/2014 | Wattebled et al. |
| 2014/0364824 A1 | 12/2014 | Ota et al. |
| 2015/0011388 A1 | 1/2015 | Matsumoto et al. |
| 2015/0087742 A1 | 3/2015 | Won et al. |
| 2015/0093575 A1 | 4/2015 | Naumann et al. |
| 2015/0129799 A1 | 5/2015 | Kobayashi et al. |
| 2015/0137546 A1 | 5/2015 | Gaudig |
| 2015/0198339 A1 | 7/2015 | Jeon |
| 2015/0283284 A1 | 10/2015 | Azad et al. |
| 2016/0108227 A1 | 4/2016 | Wattebled et al. |
| 2016/0151531 A1 | 6/2016 | Lee et al. |
| 2016/0184799 A1 | 6/2016 | Lee et al. |
| 2018/0037686 A1 | 2/2018 | Lee et al. |
| 2018/0050321 A1 | 2/2018 | Lee et al. |
| 2018/0056274 A1 | 3/2018 | Lee et al. |
| 2018/0079847 A1 | 3/2018 | Lee et al. |
| 2018/0265645 A1 | 9/2018 | Nam et al. |
| 2018/0265646 A1 | 9/2018 | Nam et al. |

FOREIGN PATENT DOCUMENTS

| | | |
|---|---|---|
| CN | 101133100 A | 2/2008 |
| CN | 102197057 A | 9/2011 |
| CN | 102666670 A | 9/2012 |
| CN | 102762616 A | 10/2012 |
| CN | 103179931 A | 6/2013 |
| CN | 104024291 A | 9/2014 |
| CN | 104284921 A | 1/2015 |
| CN | 104603159 A | 5/2015 |
| EP | 0555692 A1 | 8/1993 |
| EP | 0615736 A1 | 9/1994 |
| EP | 0644211 A1 | 3/1995 |
| EP | 0744435 A1 | 11/1996 |
| EP | 1400556 A1 | 3/2004 |
| EP | 1637105 A1 | 3/2006 |
| EP | 1730218 B1 | 12/2010 |
| EP | 3248990 A1 | 11/2017 |
| EP | 3260485 A1 | 12/2017 |
| EP | 2797566 B1 | 6/2019 |
| JP | H06313042 A | 11/1994 |
| JP | H09124879 A | 5/1997 |
| JP | H10139916 A | 5/1998 |
| JP | H10251309 A | 9/1998 |
| JP | H11071425 A | 3/1999 |
| JP | H11156188 A | 6/1999 |
| JP | 2005154758 A | 6/2005 |
| JP | 2006116535 A | 5/2006 |
| JP | 20070012623 A | 1/2007 |
| JP | 3913867 B2 | 5/2007 |
| JP | 2007314794 A | 12/2007 |
| JP | 2009227885 A | 10/2009 |
| JP | 2011511086 A | 4/2011 |
| JP | 5336704 B2 | 11/2013 |
| JP | 2014098172 A | 5/2014 |
| JP | 2014514128 A | 6/2014 |
| JP | 2014514432 A | 6/2014 |
| JP | 2014518716 A | 8/2014 |
| JP | 2014523452 A | 9/2014 |
| JP | 2015503655 A | 2/2015 |
| JP | 2015150059 A | 8/2015 |
| JP | 2015213911 A | 12/2015 |
| KR | 910008293 B1 | 10/1991 |
| KR | 930007272 B1 | 8/1993 |
| KR | 100269980 B1 | 10/2000 |
| KR | 20050022813 A | 3/2005 |
| KR | 20060015498 A | 2/2006 |
| KR | 20060023116 A | 3/2006 |
| KR | 20090042828 A | 4/2009 |
| KR | 20090123904 A | 12/2009 |
| KR | 20110092236 A | 8/2011 |
| KR | 20120102088 A | 9/2012 |
| KR | 20130120300 A | 11/2013 |
| KR | 20140054324 A | 5/2014 |
| KR | 20140056225 A | 5/2014 |
| KR | 20140094536 A | 7/2014 |
| KR | 20140095569 A | 8/2014 |
| KR | 20140102264 A | 8/2014 |
| KR | 20140107347 A | 9/2014 |
| KR | 20150016126 A | 2/2015 |
| KR | 20150040476 A | 4/2015 |
| KR | 20150084371 A | 7/2015 |
| KR | 20150116418 A | 10/2015 |
| KR | 20150143624 A | 12/2015 |
| KR | 101582241 B1 | 1/2016 |
| KR | 20160010517 A | 1/2016 |
| WO | 8703208 A1 | 6/1987 |
| WO | 2004096304 A1 | 11/2004 |
| WO | 2005027986 A1 | 3/2005 |
| WO | 2005092956 A1 | 10/2005 |
| WO | 2006069732 A1 | 7/2006 |
| WO | 2011026876 A1 | 3/2011 |
| WO | 2013099174 A1 | 7/2013 |
| WO | 2014167040 A1 | 10/2014 |
| WO | 2014168858 A1 | 10/2014 |
| WO | 2014168871 A1 | 10/2014 |

OTHER PUBLICATIONS

Extended European Search Report including Written Opinion for Application No. EP16890123.9 dated Sep. 7, 2018.
Kabiri, K., et al.., "Novel approach to highly porous superabsorbent hydrogels: synergistic effect of porogens on porosity and swelling rate." Polymer International, vol. 52, Jan. 7, 2003, pp. 1158-1164.
Kabiri, Kourosh, et al. "Porous Superabsorbent Hydrogel Composites: Synthesis, Morphology and Swelling Rate." Macromolecular Materials and Engineering, Apr. 20, 2004, vol. 289, pp. 653-661.
Odian, George, "Principle of Polymerization." Second Edition, (Wiley, 1981), p. 203.
Schwalm, Reinhold, "UV Coatings: Basics, Recent Developments and New Applications." Elservier Science, Dec. 21, 2006, p. 115.
Search report from International Application No. PCT/KR2016/003793, dated Dec. 22, 2016.
Search report from International Application No. PCT/KR2016/003946, dated Jul. 29, 2016.
Search report from International Application No. PCT/KR2016/003948, dated Jul. 27, 2016.
Search report from International Application No. PCT/KR2016/005809, dated Aug. 24, 20116.
Search report from International Application No. PCT/KR2016/006202, dated Sep. 12, 2016.
Search report from International Application No. PCT/KR2016/013286, dated Mar. 6, 2017.
Third Party Observation for Application No. 16811871.9 dated Jan. 3, 2020, 7 pages.
Third Party Observation for Application No. 16890123.9 dated Jan. 3, 2020, 4 pages.
Third Party Observation for Application No. EP16890123.9 dated Jul. 10, 2018.
Third Party Observation for Application No. PCT/KR2016/003946 dated Oct. 31, 2017.
Third Party Observation for Application No. PCT/KR2016/003948 dated Oct. 13, 2017.

(56) References Cited

OTHER PUBLICATIONS

Third Party Observation for Application No. PCT/KR2016/013286 dated Jun. 25, 2018.
Third Party Observation for PCT/KR2016/006202 dated Oct. 16, 2017.
Decision of Dec. 15, 2003 of the Boards of Appeal of the European Patent Office for Application No. 92115510.7. (2003). 23 pgs.

[FIG. 1]
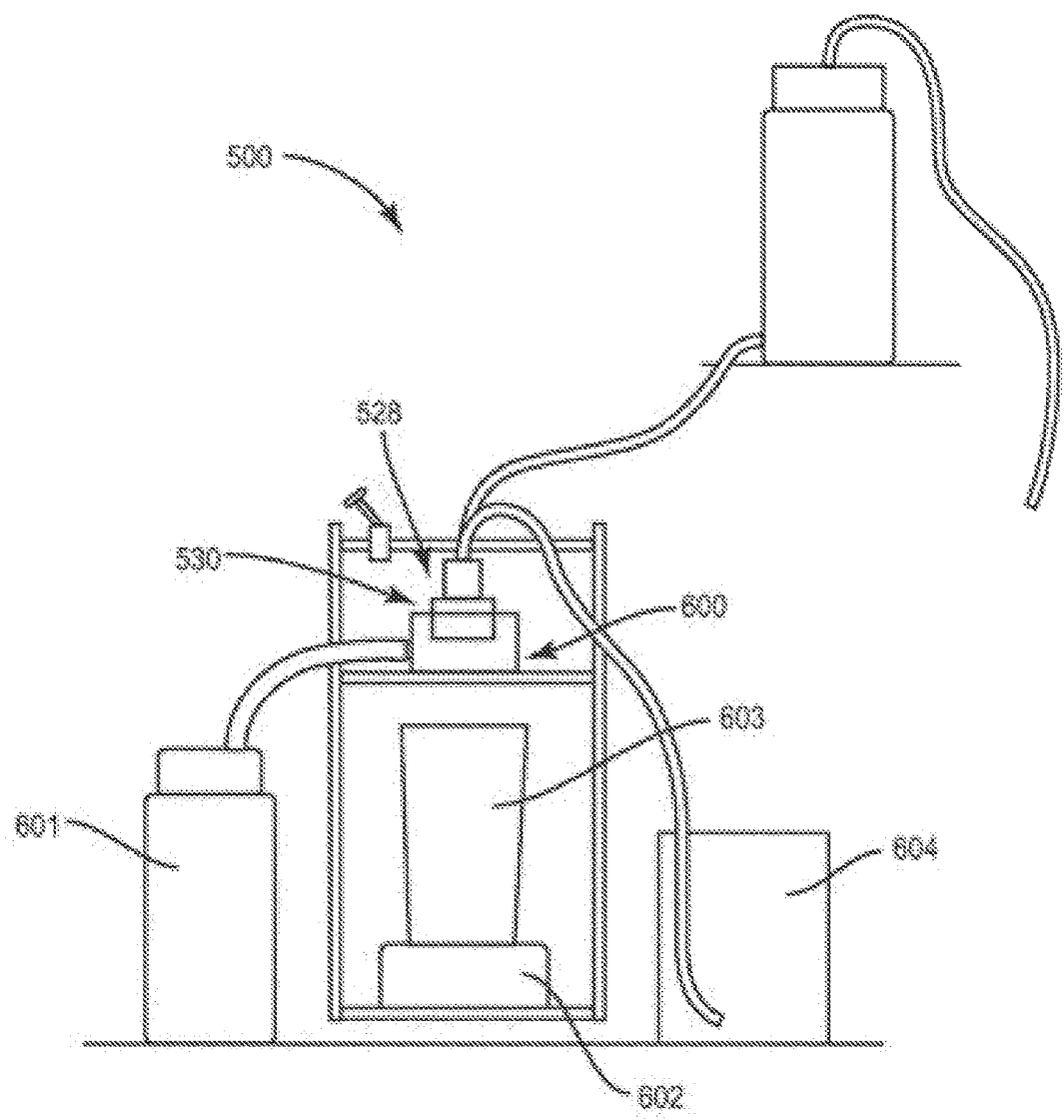

[FIG. 2]
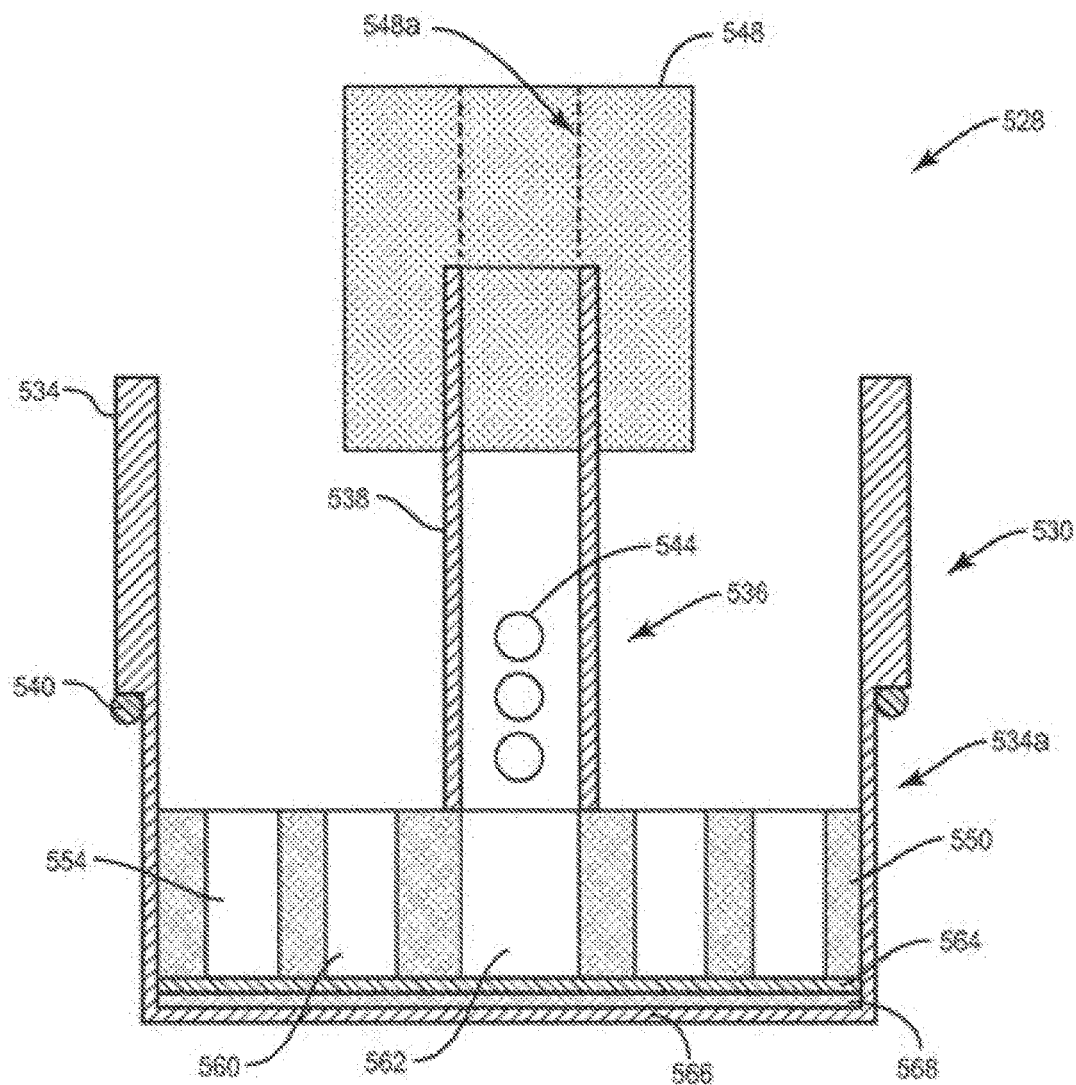

[FIG. 3]
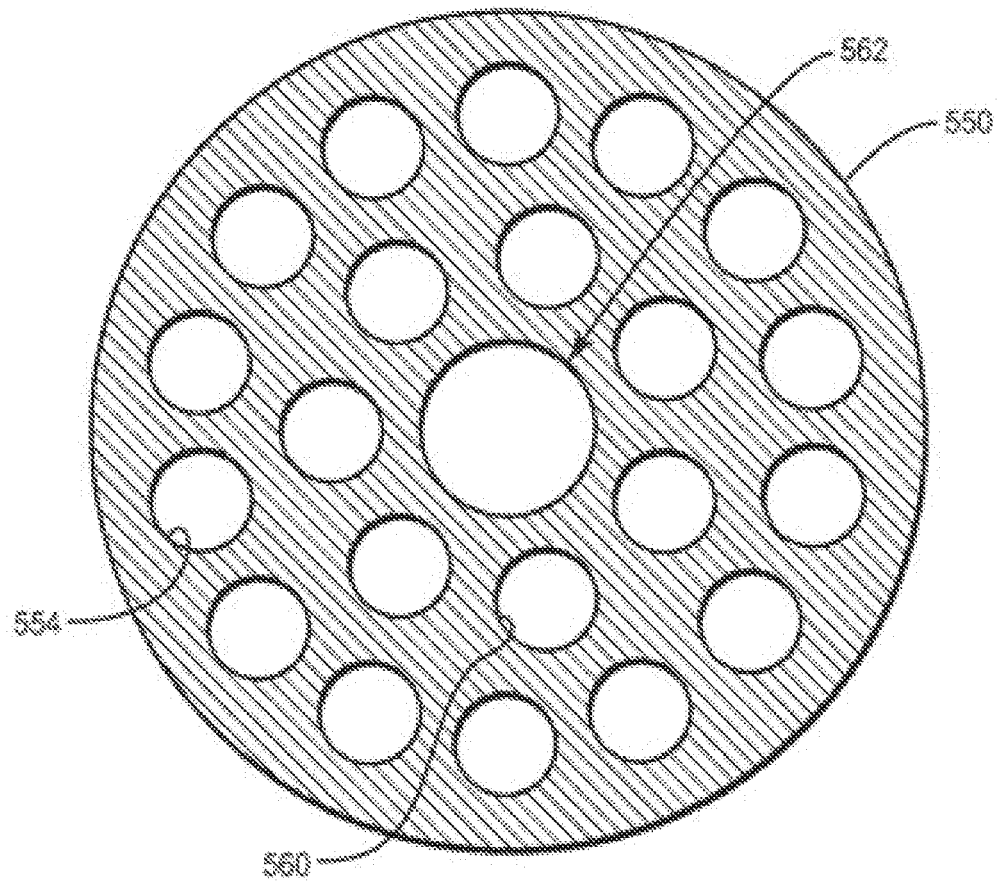

METHOD FOR PREPARING SUPERABSORBENT POLYMER, AND SUPERABSORBENT POLYMER PREPARED THEREBY

CROSS-REFERENCE TO RELATED APPLICATION

The present application is a divisional of U.S. patent application Ser. No. 15/556,083 filed Sep. 6, 2017, which is a national phase entry under 35 U.S.C. § 371 of International Application No. PCT/KR2016/003946, filed Apr. 15, 2016, claiming priority from Korean Patent Application No. 10-2015-0095926, filed Jul. 6, 2015, all of which are incorporated herein by reference.

TECHNICAL FIELD

The present invention relates to a method of preparing a superabsorbent polymer, in which deterioration of its physical properties after pulverization is minimized, and a superabsorbent polymer prepared thereby.

BACKGROUND ART

A superabsorbent polymer (SAP) is a synthetic polymeric material capable of absorbing moisture from about 500 to 1000 times its own weight. Various manufacturers have denominated it as different names, such as SAM (Super Absorbency Material), AGM (Absorbent Gel Material), etc. Since such superabsorbent polymers started to be practically applied in sanitary products, now they have been widely used not only for hygiene products such as disposable diapers for children, sanitary napkins, etc., but also for water retaining soil products for gardening, water stop materials for the civil engineering and construction, sheets for raising seedling, fresh-keeping agents for food distribution fields, materials for poultice, etc.

In most cases, these superabsorbent polymers have been widely used in the field of hygienic materials such as diapers, sanitary napkins, etc. For these applications, the superabsorbent polymers are required to exhibit a high absorption rate with respect to moisture, etc., and also to exhibit an absorption rate above a predetermined level even under an external pressure.

In particular, superabsorbent polymers have been required to have higher absorption performances with recent slimness of sanitary materials such as diapers, sanitary napkins, etc. In order to allow the body fluid to rapidly spread and to be rapidly absorbed in the sanitary material at the same time, simultaneous enhancement of liquid permeability and absorption rate which are incompatible physical properties of superabsorbent polymers is emerging as an important issue.

Therefore, for simultaneous enhancement of liquid permeability and absorption rate of superabsorbent polymers, attempts have been made to improve liquid permeability of superabsorbent polymers by allowing inorganic particles such as silica, etc. to exist between the superabsorbent polymer particles.

However, when a large amount of inorganic particles is used for sufficient improvement of the liquid permeability of superabsorbent polymers, there is a problem in that the absorption rate under a pressure is lowered. Further, during processes of pulverizing and size-sorting the superabsorbent polymers, inorganic particles added to the superabsorbent polymers are separated therefrom, and thus, it is difficult to improve the liquid permeability at a desired level.

Accordingly, there is an urgent need for studies to improve the liquid permeability and absorption rate of superabsorbent polymers without the above problems.

DISCLOSURE

Technical Problem

The present invention provides a method of preparing a superabsorbent polymer, in which deterioration of its physical properties after pulverization is minimized, and a superabsorbent polymer prepared thereby.

Technical Solution

According to an embodiment of the present invention, provided is a method of preparing a superabsorbent polymer, the method including the steps of: performing crosslinking polymerization of a monomer mixture including water-soluble ethylene-based unsaturated monomers having acidic groups which are at least partially neutralized, in the presence of an internal crosslinking agent to form a water-containing gel polymer; drying, pulverizing, and size-sorting the water-containing gel polymer to form a base polymer powder; and additionally crosslinking the surface of the base polymer powder in the presence of a thickener having a weight average molecular weight of 300 g/mol to 1,000,000 g/mol and a surface crosslinking agent to form a surface-crosslinked layer.

In the step of forming the surface-crosslinked layer, the thickener may be one or more selected from polysaccharides and polymers containing hydroxyl groups. More specifically, the polysaccharides may be one or more selected from gum-based thickeners selected from the group consisting of xanthan gum, arabic gum, karaya gum, tragacanth gum, ghatti gum, guar gum, locust bean gum, and psyllium seed gum, and cellulose-based thickeners selected from the group consisting of hydroxypropylmethylcellulose, carboxymethylcellulose, methylcellulose, hydroxymethylcellulose, hydroxyethylcellulose, hydroxypropylcellulose, hydroxyethylmethylcellulose, hydroxymethylpropylcellulose, hydroxyethylhydroxypropylcellulose, ethylhydroxyethylcellulose, and methylhydroxypropylcellulose. The polymers containing hydroxyl groups may be one or more selected from polyethylene glycol and polyvinyl alcohol.

The thickener may be used in an amount of 0.01 to 1 parts by weight with respect to 100 parts by weight of the base polymer powder, thereby minimizing deterioration of physical properties of the superabsorbent polymer after pulverization.

Meanwhile, in the step of forming the surface-crosslinked layer, the surface crosslinking agent may be one or more polyols selected from the group consisting of ethylene glycol, propylene glycol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol and glycerol; or one or more carbonate-based compounds selected from the group consisting of ethylene carbonate and propylene carbonate.

Such surface crosslinking agent may be used in an amount of 0.01 to 4 parts by weight with respect to 100 parts by weight of the base polymer powder.

Further, in the step of forming the surface-crosslinked layer, the surface-crosslinked layer may be formed in the presence of an inorganic material of less than 0.5 parts by weight with respect to 100 parts by weight of the base polymer powder. The preparation method according to an embodiment may provide a superabsorbent polymer capable of showing excellent liquid permeability and absorption rate without using an inorganic material or only by using a small amount of an inorganic material within the above-described range.

The preparation method according to an embodiment may further include the step of pulverizing the surface-crosslinked superabsorbent polymer.

Meanwhile, according to another embodiment of the present invention, provided is a superabsorbent polymer, including a base polymer powder including a crosslinking polymer of water-soluble ethylene-based unsaturated monomers having acidic groups which are at least partially neutralized; and a surface-crosslinked layer formed on the base polymer powder, wherein a GBP reduction rate of the following Equation 1 is −55% to 0%:

GBP reduction rate (%)=$\{(G_1-G_0)/G_0\}*100$    [Equation 1]

wherein $G_0$ is an initial gel bed permeability of the superabsorbent polymer, and $G_1$ is a gel bed permeability of the superabsorbent polymer having a particle size of 300 μm to 600 μm, which is obtained by pulverizing the superabsorbent polymer using a ball mill under 300 rpm for 20 minutes and then size-sorting the pulverized superabsorbent polymer.

Further, the superabsorbent polymer may have a reduction rate of absorbency under load of the following Equation 2 of −4% to 0% because reduction of the absorbency under load after pulverization may be minimized:

Reduction rate of absorbency under load (%)=$\{(A_1-A_0)/A_0\}*100$    [Equation 2]

wherein $A_0$ is an initial absorbency under load of the superabsorbent polymer, on which the surface-crosslinked layer is formed, as calculated by the following Calculation Formula 4, and $A_1$ is an absorbency under load of the superabsorbent polymer having a particle size of 300 μm to 600 μm, which is obtained by pulverizing the superabsorbent polymer using a ball mill under 300 rpm for 20 minutes and then size-sorting the pulverized superabsorbent polymer, as calculated by the following Calculation Formula 4, 5 min gel-vac-AUL(g/g)= $[W_6(g)-W_5(g)]/W_0(g)$    [Calculation Formula 4]

wherein $W_0$ (g) is an initial weight (g) of the superabsorbent polymer, $W_5$ (g) is the sum of the weight of the superabsorbent polymer and a weight of an apparatus capable of providing a load for the superabsorbent polymer, and $W_6$ (g) is the sum of the weight of the superabsorbent polymer, which is measured after allowing the superabsorbent polymer to absorb a physiological saline solution under a load (0.3 psi) for 5 minutes and removing residual liquid using a vacuum apparatus, and the weight of the apparatus capable of providing a load for the superabsorbent polymer.

Additionally, the superabsorbent polymer may exhibit excellent absorption performances even after pulverization. Specifically, the superabsorbent polymer having a particle size of 300 μm to 600 μm, which is obtained by pulverizing the superabsorbent polymer using a ball mill under 300 rpm for 20 minutes and then size-sorting the pulverized superabsorbent polymer, may exhibit characteristics that centrifuge retention capacity (CRC) in a physiological saline solution is 30 g/g to 32 g/g, absorbency under load (AUL) of 0.9 psi in the physiological saline solution is 20 to 22 g/g, free swell gel bed permeability (GBP) in the physiological saline solution is 12 darcy to 100 darcy, and absorbency under load (5 min gel-vac-AUL) of the superabsorbent polymer, as measured after swelling the superabsorbent polymer in the physiological saline solution under a load of 0.3 psi for 5 minutes and removing residual liquid under vacuum, is 17 g/g to 19 g/g.

Effect of the Invention

A superabsorbent polymer according to an embodiment of the present invention exhibits minimized deterioration of physical properties after pulverization, thereby having not only excellent basic absorption performances but also superior liquid permeability and absorption rate.

BRIEF DESCRIPTION OF DRAWINGS

FIGS. 1 to 3 are schematic views of an exemplary apparatus for measuring gel bed permeability and components provided in the apparatus.

DETAILED DESCRIPTION OF THE EMBODIMENTS

Hereinafter, a method of preparing a superabsorbent polymer according to a specific embodiment of the present invention and a superabsorbent polymer prepared thereby will be described in detail.

According to an embodiment of the present invention, provided is a method of preparing a superabsorbent polymer, the method including the steps of: performing crosslinking polymerization of a monomer mixture including water-soluble ethylene-based unsaturated monomers having acidic groups which are at least partially neutralized, in the presence of an internal crosslinking agent to form a water-containing gel polymer; drying, pulverizing, and size-sorting the water-containing gel polymer to form a base polymer powder; and additionally crosslinking the surface of the base polymer powder in the presence of a thickener having a weight average molecular weight of 300 g/mol to 1,000,000 g/mol and a surface crosslinking agent to form a surface-crosslinked layer.

Experimental results of the present inventors confirmed that when the surface-crosslinked layer of the superabsorbent polymer is formed in the presence of the thickener capable of increasing viscous property or viscosity, deterioration of specific physical properties after fragmentation or pulverization may be minimized, thereby completing the present invention. Particularly, among various required physical properties of the superabsorbent polymer, liquid permeability is rapidly reduced after fragmentation or pulverization of the superabsorbent polymer, but the preparation method according to an embodiment may provide a superabsorbent polymer exhibiting excellent liquid permeability even after fragmentation or pulverization.

The preparation method according to an embodiment may provide the superabsorbent polymer in the same manner as in methods known in the art to which the present invention pertains, except that the thickener capable of increasing viscous property or viscosity is used in the step of forming the surface-crosslinked layer.

Hereinafter, the method of preparing the superabsorbent polymer according to an embodiment will be described in more detail.

In the preparation method according to an embodiment, as the water-soluble ethylene-based unsaturated monomer, any one or more selected from the group consisting of an anionic monomer such as acrylic acid, (meth)acrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, and salts thereof; a nonionic hydrophilic monomer such as (meth)acrylamide, N-substituted (meth)acrylate, 2-hydroxyethyl (meth)acrylate, 2-hydroxypropyl(meth)acrylate, methoxy polyethylene glycol (meth)acrylate, or polyethylene glycol (meth)acrylate; and an amino group-containing unsaturated monomer such as (N,N)-dimethylaminoethyl(meth)acrylate or (N,N)-dimethylaminopropyl(meth)acrylamide, and a quaternary compound thereof may be used. Among them, acrylic acid or salts thereof, for example, acrylic acid which is at least partially neutralized, and/or alkali metal salts thereof such as sodium salts thereof may be used, and it is possible to prepare a superabsorbent polymer having superior physical properties by using these monomers. When the alkali metal salt of acrylic acid is used as the monomer, acrylic acid may be used after being neutralized with a basic compound such as caustic soda (NaOH). In this regard, a neutralization degree of the water-soluble ethylene-based unsaturated monomer may be controlled in the range of about 50% to about 95% or about 70% to about 85%. When the water-soluble ethylene-based unsaturated monomer is neutralized within the above range, it is possible to provide a superabsorbent polymer having excellent centrifuge retention capacity without concern about precipitation.

In the monomer mixture including the water-soluble ethylene-based unsaturated monomers, the concentration of the water-soluble ethylene-based unsaturated monomer may be about 20% by weight to about 60% by weight, or about 40% by weight to about 50% by weight with respect to a total weight of the monomer mixture including raw materials described below and a solvent, and the concentration may be properly controlled, in consideration of a polymerization time and reaction conditions. However, if the monomer concentration is too low, the yield of the superabsorbent polymer may become low and an economic problem may occur. On the contrary, if the concentration is too high, there is a process problem that a part of the monomers is precipitated, or pulverization efficiency is lowered upon pulverization of the polymerized water-containing gel polymer, and the physical properties of the superabsorbent polymer may be deteriorated.

As the internal crosslinking agent to introduce a basic crosslinked structure into the base polymer powder, any internal crosslinking agent having a crosslinkable functional group which has been generally used in the preparation of the superabsorbent polymer may be used without limitation. However, to further improve physical properties of the superabsorbent polymer by introducing a proper crosslinked structure into the base polymer powder, a multifunctional acrylate-based compound having a plurality of ethylene oxide groups may be used as the internal crosslinking agent. More specific examples of the internal crosslinking agent may include one or more selected from the group consisting of polyethylene glycol diacrylate (PEGDA), glycerin diacrylate, glycerin triacrylate, non-modified or ethoxylated trimethylol propane triacrylate (TMPTA), hexanediol diacrylate, and triethylene glycol diacrylate. The internal crosslinking agent may be included in an amount of about 0.01% by weight to about 0.5% by weight with respect to the monomer mixture, thereby crosslinking the polymerized polymer.

In addition, the monomer mixture may further include a polymerization initiator which is generally used in the preparation of the superabsorbent polymer.

Specifically, the polymerization initiator may be a thermal polymerization initiator or a photo-polymerization initiator by UV irradiation, depending on a polymerization method. However, even though the photo-polymerization is performed, a certain amount of heat may be generated by UV irradiation, etc., and also generated with exothermic polymerization reaction. Therefore, the thermal polymerization initiator may be further included.

As the photo-polymerization initiator, a compound capable of forming radicals by a light such as UV may be used without limitations in the constitution.

For example, one or more selected from the group consisting of benzoin ether, dialkyl acetophenone, hydroxyl alkylketone, phenyl glyoxylate, benzyl dimethyl ketal, acyl phosphine, and α-aminoketone may be used as the photo-polymerization initiator. Meanwhile, as the specific example of acyl phosphine, commercial lucirin TPO, namely, 2,4,6-trimethyl-benzoyl-trimethyl phosphine oxide may be used. More various photo-polymerization initiators are well disclosed in "UV Coatings: Basics, Recent Developments and New Application (Elsevier, 2007)" written by Reinhold Schwalm, p115, however, they are not limited to the above described examples.

The photo-polymerization initiator may be included in an amount of about 0.01% by weight to about 1.0% by weight with respect to the monomer mixture. If the concentration of the photo-polymerization initiator is too low, the polymerization rate may become low. If the concentration of the photo-polymerization initiator is too high, a molecular weight of the superabsorbent polymer may become low and its physical properties may not be uniform.

Further, one or more selected from the group consisting of persulfate-based initiators, azo-based initiators, hydrogen peroxide, and ascorbic acid may be used as the thermal polymerization initiator. Specific examples of the persulfate-based initiators may include sodium persulfate ($Na_2S_2O_8$), potassium persulfate ($K_2S_2O_8$), ammonium persulfate (($NH_4)_2S_2O_8$), etc. Examples of the azo-based initiators may include 2,2-azobis(2-amidinopropane)dihydrochloride, 2,2-azobis-(N,N-dimethylene)isobutyramidine dihydrochloride, 2-(carbamoylazo)isobutylonitrile, 2,2-azobis(2-[2-imidazolin-2-yl]propane)dihydrochloride, 4,4-azobis-(4-cyanovaleric acid), etc. More various thermal polymerization initiators are well-disclosed in 'Principle of Polymerization (Wiley, 1981)' written by Odian, p203, however, they are not limited to the above described examples.

The thermal polymerization initiator may be included in an amount of about 0.001% by weight to about 0.5% by weight with respect to the monomer mixture. If the concentration of the thermal polymerization initiator is too low, additional thermal polymerization hardly occurs, and thus the addition effect of the thermal polymerization initiator may not be sufficiently obtained. If the concentration of the thermal polymerization initiator is too high, the molecular weight of the superabsorbent polymer may become low and its physical properties may not be uniform.

The monomer mixture may further include an additive such as a thickener, a plasticizer, a preservation stabilizer, an antioxidant, etc., if necessary.

The raw materials such as the above-described water-soluble ethylene-based unsaturated monomer, photo-polymerization initiator, thermal polymerization initiator, internal crosslinking agent, and additive may be prepared in the form of being dissolved in a solvent.

In this regard, as the solvent, any solvent may be used without limitations in the constitution as long as it is able to dissolve the above ingredients, and for example, one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate and N,N-dimethylacetamide may be used in combination.

The solvent may be included in a remaining amount excluding the above described components from the total weight of the monomer mixture.

Meanwhile, the method of forming the water-containing gel polymer by thermal polymerization or photo-polymerization of the monomer composition is not particularly limited to the constitution, as long as it is a method generally used.

Specifically, the polymerization method may be largely classified into the thermal polymerization and the photo-polymerization according to a polymerization energy source. The thermal polymerization may be carried out in a reactor like a kneader equipped with agitating spindles, whereas the photo-polymerization may be carried out in a reactor equipped with a movable conveyor belt. The above-described polymerization method is an example only, and the present invention is not limited thereto.

For example, as described above, thermal polymerization is performed by providing hot air to a reactor like a kneader equipped with the agitating spindles or by heating the reactor to obtain the water-containing gel polymer. At this time, the water-containing gel polymer thus obtained may have a size of centimeters or millimeters when it is discharged from the outlet of the reactor, according to the type of agitating spindles equipped in the reactor. Specifically, the water-containing gel polymer may be obtained in various forms according to the concentration of the monomer mixture fed thereto, the feeding speed, etc. Generally, the water-containing gel polymer having a weight average particle size of about 2 mm to about 50 mm may be obtained.

Further, as described above, when the photo-polymerization is carried out in a reactor equipped with a movable conveyor belt, the water-containing gel polymer generally obtained may be a water-containing gel polymer of a sheet-type having a width of the belt. In this regard, the thickness of the polymer sheet may vary according to the concentration of the monomer composition fed thereto and the feeding speed, and the feeding speed of the monomer composition is preferably controlled so that the sheet-type polymer having a thickness of about 0.5 cm to about 5 cm is obtained. If the monomer composition is fed such that the thickness of the sheet-type polymer becomes too thin, the production efficiency becomes low, which is not preferred. If the thickness of the sheet-type polymer exceeds 5 cm, the polymerization reaction may not uniformly occur throughout the polymer due to the excessively high thickness.

In this regard, the water-containing gel polymer thus obtained by the method may have generally a water content of about 40% by weight to about 80% by weight. Meanwhile, the term "water content", as used herein, means a water content in the total weight of the water-containing gel polymer, which is obtained by subtracting the weight of the dry polymer from the weight of the water-containing gel polymer. Specifically, the water content is defined as a value calculated by measuring the weight loss according to evaporation of water in the polymer during the drying process of increasing the temperature of the polymer with infrared heating. In this regard, the water content is measured under the drying conditions which are determined as follows; the temperature is increased from room temperature to about 180° C. and then the temperature is maintained at 180° C., and the total drying time is determined as 20 minutes, including 5 minutes for the temperature rising step.

After crosslinking polymerization of the monomers, drying, pulverizing, and size-sorting processes may be performed to obtain the base polymer powder. Through the pulverizing and size-sorting processes, the base polymer powder and the superabsorbent polymer obtained therefrom are suitably prepared and provided such that they have a particle size of about 150 µm to about 850 µm. More specifically, at least about 95% by weight of the base polymer powder and the superabsorbent polymer obtained therefrom may have a particle size of about 150 µm to about 850 µm, and fine powder having a particle size of less than about 150 µm may be less than about 3% by weight.

As such, when particle size distributions of the base polymer powder and the superabsorbent polymer are controlled within the preferred range, the superabsorbent polymer finally prepared may exhibit the above-described physical properties and superior liquid permeability.

Meanwhile, the methods of performing the drying, pulverizing, and size-sorting will be described in more detail as follows.

First, in drying the water-containing gel polymer, a coarse pulverization process may be further carried out before drying in order to increase the efficiency of the drying process, if necessary.

There is no limitation in the constitution of a milling machine to be used. Specifically, any one device selected from the group consisting of a vertical pulverizer, a turbo cutter, a turbo grinder, a rotary cutter mill, a cutter mill, a disc mill, a shred crusher, a crusher, a chopper, and a disc cutter may be used, but it is not limited thereto.

In this regard, the coarse pulverization may be carried out such that the water-containing gel polymer has a particle size of about 2 mm to about 10 mm.

Due to the high water content, it is technically not easy to pulverize the water-containing gel polymer into a particle size of less than 2 mm, and a phenomenon of agglomeration between the pulverized particles may occur. Meanwhile, when the particle size is larger than 10 mm, the effect of increasing the efficiency of the subsequent drying process may be unsatisfactory.

The water-containing gel polymer coarsely pulverized as above or the water-containing gel polymer immediately after polymerization without the coarse pulverizing step is subjected to a drying step. In this case, a drying temperature of the drying step may be about 150° C. to about 250° C. When the drying temperature is lower than 150° C., it is likely that the drying time becomes too long or the physical properties of the superabsorbent polymer finally formed are deteriorated, and when the drying temperature is higher than 250° C., only the surface of the polymer is dried, and thus it is likely that fine powder is generated during the subsequent pulverizing step and the physical properties of the superabsorbent polymer finally formed are deteriorated. Therefore, the drying step may be preferably carried out at a temperature of about 150° C. to about 200° C., and more preferably at a temperature of about 160° C. to about 180° C.

Meanwhile, the drying time may be about 20 minutes to about 90 minutes in consideration of process efficiency, etc., but is not limited thereto.

In the drying step, the drying method may also be selected and used without any limitation in the constitution, as long as it is a method generally used for drying the water-containing gel polymer. Specifically, the drying step may be carried out by a method such as hot air supply, infrared irradiation, microwave irradiation, or ultraviolet irradiation. When the drying step as above is finished, the water content of the polymer may be about 0.1% by weight to about 10% by weight.

Subsequently, the dried polymer obtained through the drying step is subjected to a pulverization step.

The polymer powder obtained through the pulverizing step may have a particle size of about 150 μm to about 850 μm. Specific examples of a milling machine used to achieve the above particle size may include a ball mill, a pin mill, a hammer mill, a screw mill, a roll mill, a disc mill, a jog mill, etc., but is not limited thereto.

Also, in order to manage the physical properties of the superabsorbent polymer powder finally commercialized after the pulverization step, a separate process of sorting the polymer powder obtained after the pulverization depending on the particle size may be performed. Preferably, a polymer having a particle size of about 150 μm to about 850 μm is sorted, and only the polymer powder having such a particle size is subjected to the surface crosslinking reaction and finally commercialized.

Meanwhile, after the process of forming the above-described base polymer powder, the surface of the base polymer powder may be further crosslinked in the presence of the above-described thickener and surface crosslinking agent to form a surface-crosslinked layer, thereby preparing a superabsorbent polymer.

When the surface of the base polymer powder is further crosslinked in the presence of the thickener, deterioration of the physical properties may be minimized even after pulverization.

In the preparation method of an embodiment, a thickener having a weight average molecular weight of 300 g/mol to 1,000,000 g/mol, 300 g/mol to 800,000 g/mol, or 400 g/mol to 700,000 g/mol may be used. The thickener having a molecular weight within the range may minimize structural deformation of the surface-crosslinked layer and deterioration of physical properties after pulverization due to sufficient viscous property or viscosity-increasing effect.

More specifically, to achieve the above-described effects, when a polysaccharide is used as the thickener, a polysaccharide having a weight average molecular weight of 300 g/mol to 1,000,000 g/mol, 50,000 g/mol to 1,000,000 g/mol, 100,000 g/mol to 900,000 g/mol, or 400,000 g/mol to 800,000 g/mol may be used, and when a polymer containing hydroxyl groups is used, a polymer having a weight average molecular weight of 300 g/mol to 1,000,000 g/mol, 300 g/mol to 500,000 g/mol, 300 g/mol to 200,000 g/mol, or 400 g/mol to 150,000 g/mol may be used.

The term 'fragmentation', as used herein, means formation of particles having a smaller particle size by applying a physical force thereto, and may be used interchangeably with 'pulverization'.

More specifically, one or more selected from polysaccharides and polymers containing hydroxyl groups may be used as the thickener.

Of them, the polysaccharides may be gum-based thickeners and cellulose-based thickeners. Specific examples of the gum-based thickeners may include xanthan gum, arabic gum, karaya gum, tragacanth gum, ghatti gum, guar gum, locust bean gum, psyllium seed gum, etc., and specific examples of the cellulose-based thickeners may include hydroxypropylmethylcellulose, carboxymethylcellulose, methylcellulose, hydroxymethylcellulose, hydroxyethylcellulose, hydroxypropylcellulose, hydroxyethylmethylcellulose, hydroxymethylpropylcellulose, hydroxyethylhydroxypropylcellulose, ethylhydroxyethylcellulose, methylhydroxypropylcellulose, etc.

Meanwhile, specific examples of the polymers containing hydroxyl groups may include polyethylene glycol, polyvinyl alcohol, etc.

The thickener may be used in an amount of 0.01 to 1 parts by weight with respect to 100 parts by weight of the base polymer powder, thereby effectively preventing deterioration of physical properties of the superabsorbent polymer after pulverization.

The surface-crosslinked layer may be formed by using a surface crosslinking agent which has been used in the preparation of the superabsorbent polymer. As the surface crosslinking agent, any surface crosslinking agent known in the art to which the present invention pertains may be used without limitation. More specific examples thereof may include polyols such as ethylene glycol, propylene glycol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol, glycerol, etc.; or carbonate-based compounds such as ethylene carbonate, propylene carbonate, etc. Such surface crosslinking agent may be used in an amount of 0.01 to 4 parts by weight with respect to 100 parts by weight of the base polymer powder.

Meanwhile, in the art to which the present invention pertain, a method of using an inorganic material during the surface-crosslinking process for simultaneous improvement of the liquid permeability and absorption rate of the superabsorbent polymer is known. However, when a large amount of the inorganic material is used for sufficient improvement of the liquid permeability and absorption rate, an absorption rate under load may be reduced. Further, during pulverization of the superabsorbent polymer which is performed after the surface crosslinking process, the inorganic material may be separated, and therefore, it is difficult to sufficiently achieve the effect of the inorganic material.

However, in the preparation method of an embodiment, the thickener is used during formation of the surface-crosslinked layer, thereby effectively preventing separation of the inorganic material from the superabsorbent polymer. Accordingly, in the preparation method according to an embodiment, simultaneous improvement of liquid permeability and absorption rate may be sufficiently achieved, even though a very small amount of the inorganic material is used.

For example, in the surface crosslinking process, the surface crosslinking reaction may be performed by adding the inorganic material of less than 0.50 parts by weight, less than 0.30 parts by weight, less than 0.10 parts by weight, or less than 0.07 parts by weight with respect to 100 parts by weight of the base polymer powder. The superabsorbent polymer prepared by adding a small amount of the inorganic material may exhibit excellent liquid permeability and absorption rate without reduction of absorption rate under load which is caused by using a large amount of the inorganic material. In the surface crosslinking process, the inorganic material essentially employed in the known method may be omitted. Thus, a lowest limit of the content of the inorganic material may be 0 part by weight.

If the inorganic material is added in the surface crosslinking process, one or more inorganic materials selected from the group consisting of silica, clay, alumina, a silica-alumina composite, titania, zinc oxide, and aluminum sulfate may be added. These inorganic materials may be used in a powdery form or in a liquid form, and in particular, alumina powder, silica-alumina powder, titania powder, or a nanosilica solution may be used.

Further, in the surface crosslinking process, when the surface crosslinking is performed by adding a multivalent metal cation instead of the inorganic material or together with the inorganic material, the surface crosslinked structure of the superabsornet polymer may be further optimized. This may be because the metal cation forms a chelate with a carboxyl group (COOH) of the superabsorbent polymer to further reduce a crosslinking distance.

There is no limitation in the method of adding the thickener and the surface crosslinking agent to the base polymer powder. For example, a method of adding and mixing the thickener and the surface crosslinking agent with the base polymer powder in a reactor, a method of spraying the thickener and the surface crosslinking agent onto the base polymer powder, and a method of continuously mixing the base polymer powder and the thickener and the surface crosslinking agent while providing them to a mixer that is continuously operated may be used.

When the thickener and the surface crosslinking agent are added thereto, water and methanol may be further mixed therewith. When water and methanol are added thereto, there is an advantage that the surface crosslinking agent may be evenly dispersed in the base polymer powder. At this time, amounts of water and methanol to be added may be regulated for the purposes of inducing a uniform dispersion of the surface crosslinking agent, preventing an agglomeration phenomenon of the base polymer powder, and optimizing a surface penetration depth of the crosslinking agent.

The surface crosslinking reaction may be carried out by heating the base polymer powder, to which the surface crosslinking agent is applied, at about 100° C. or higher. Particularly, in order to prepare the superabsorbent polymer having satisfactory physical properties, the surface crosslinking process may be carried out under the conditions that a maximum reaction temperature is about 160° C. or higher, or about 180° C. to 200° C., and the maximum reaction temperature may be maintained for about 20 minutes or more, or for about 20 minutes and 1 hour or less. Furthermore, the heat-up time from the reaction initiation temperature, for example, about 100° C. or higher, or about 160° C. to about 170° C., to the maximum reaction temperature may be controlled to be about 10 minutes or more, or about 10 minutes or more and 1 hour or less, and it was confirmed that the superabsorbent polymer having satisfactory physical properties may be prepared by satisfying the above conditions of the surface crosslinking process.

A means for raising the temperature for surface crosslinking reaction is not particularly limited. Heating may be performed by providing a heating medium or by directly providing a heat source. In this regard, the type of the heating medium applicable may be a hot fluid such as steam, hot air, hot oil, etc., but is not limited thereto. The temperature of the heating medium provided may be properly selected in consideration of the means of the heating medium, a heating speed, and a target temperature of heating. Meanwhile, an electric heater or a gas heater may be used as the heat source provided directly, but the heat source is not limited to these examples.

Meanwhile, after the above-described surface crosslinking process, a step of pulverizing the surface-crosslinked superabsorbent polymer may be further included.

As described above, the term 'fragmentation', as used herein, is used interchangeably with the term 'pulverization'.

The fragmentation of the superabsorbent polymer may be performed by using the milling machine used for coarse pulverization of the water-containing gel polymer or the milling machine used for pulverization of the dried water-containing gel polymer. The superabsorbent polymer powder thus obtained by pulverization may have a particle size of about 150 μm to about 850 μm. Further, the pulverized superabsorbent polymer may be further size-sorted to obtain the superabsorbent polymer having a desired particle size.

The superabsorbent polymer obtained by the above-described preparation method may exhibit minimized deterioration of physical properties even after pulverization, due to the thickener used in the surface crosslinking process. Further, even though the inorganic material is not used or a very small amount thereof is used in the surface crosslinking process, excellent liquid permeability and absorption rate may be obtained. Accordingly, the superabsorbent polymer may exhibit excellent absorption rate under load, and may effectively avoid a rewetting phenomenon due to excellent absorption rate and liquid permeability.

Meanwhile, according to another embodiment of the present invention, provided is a superabsorbent polymer obtained by the above-described preparation method. This superabsorbent polymer may include a base polymer powder including a crosslinked polymer of water-soluble ethylene-based unsaturated monomers having acidic groups which are at least partially neutralized; and a surface-crosslinked layer formed on the base polymer powder. Further, the superabsorbent polymer may have a GBP reduction rate of the following Equation 1 of −55% to 0%:

$$\text{GBP reduction rate (\%)} = \{(G_1 - G_0)/G_0\} \ast 100 \quad \text{[Equation 1]}$$

wherein $G_0$ is an initial gel bed permeability of the superabsorbent polymer having the surface-crosslinked layer, and $G_1$ is a gel bed permeability of the superabsorbent polymer having a particle size of 300 μm to 600 μm, which is obtained by pulverizing the superabsorbent polymer using a ball mill under 300 rpm for 20 minutes and then size-sorting the pulverized superabsorbent polymer.

The gel bed permeability may be measured by a method described below, and a detailed measurement method will be described below.

Meanwhile, the superabsorbent polymer of another embodiment may exhibit a very low reduction rate of absorbency under load due to fragmentation. More specifically, the superabsorbent polymer may have a reduction rate of absorbency under load of the following Equation 2 of −4% to 0%:

$$\text{Reduction rate of absorbency under load (\%)} = \{(A_1 - A_0)/A_0\} \ast 100 \quad \text{[Equation 2]}$$

wherein $A_0$ is an initial absorbency under load (5 min gel-vac-AUL calculated by Calculation Formula 4) of the superabsorbent polymer, on which the surface-crosslinked layer is formed, and $A_1$ is an absorbency under load (5 min gel-vac-AUL calculated by Calculation Formula 4) of the superabsorbent polymer having a particle size of 300 μm to 600 μm, which is obtained by pulverizing the superabsorbent polymer using a ball mill under 300 rpm for 20 minutes and then size-sorting the pulverized superabsorbent polymer.

5 min gel-vac-AUL may be measured by a method described below, and a detailed measurement method will be described below.

Additionally, the superabsorbent polymer of another embodiment may exhibit satisfactory basic absorption performances even after pulverization. More specifically, when the superabsorbent polymer is pulverized by using a ball mill under conditions of 300 rpm and 20 minutes and size-sorted to obtain the superabsorbent polymer having a particle size of 300 μm to 600 μm, and then basic absorption performances thereof was evaluated, the superabsorbent polymer may exhibit the following characteristics. That is, the pulverized superabsorbent polymer may exhibit characteristics that centrifuge retention capacity (CRC) in a physiological saline solution is 30 g/g to 32 g/g, absorbency under load (AUL) of 0.9 psi in the physiological saline solution is 20 to 22 g/g, free swell gel bed permeability (GBP) in the physiological saline solution is 12 darcy to 100 darcy, and absorbency under load (5 min gel-vac-AUL) of the superabsorbent polymer, as measured after swelling the superabsorbent polymer in the physiological saline solution under a load of 0.3 psi for 5 minutes and removing residual liquid under vacuum, is 17 g/g to 19 g/g.

The centrifuge retention capacity (CRC) in a physiological saline solution may be measured in accordance with EDANA method WSP 241.2. More specifically, the centrifuge retention capacity may be calculated by the following Calculation Formula 1, after allowing the superabsorbent polymer to absorb a physiological saline solution over 30 minutes:

$$CRC(g/g) = \{[W_2(g) - W_1(g)]/W_0(g)\} - 1 \quad \text{[Calculation Formula 1]}$$

wherein $W_0$ (g) is an initial weight (g) of the superabsorbent polymer, $W_1$ (g) is a weight of an apparatus, which is measured after draining water off at 250 G for 3 minutes using a centrifuge without the superabsorbent polymer, and $W_2$ (g) is the weight of the apparatus including the superabsorbent polymer, which is measured after immersing the superabsorbent polymer in 0.9 wt % physiological saline solution at room temperature for 30 minutes and draining water off at 250 G for 3 minutes using a centrifuge.

Further, the absorbency under load (AUL) of 0.9 psi may be measured in accordance with EDANA method WSP 242.2. More specifically, the absorbency under load may be calculated by the following Calculation Formula 2, after allowing the superabsorbent polymer to absorb a physiological saline solution under a load of about 0.9 psi over 1 hour:

$$AUL(g/g) = [W_4(g) - W_3(g)]/W_0(g) \quad \text{[Calculation Formula 2]}$$

wherein $W_0$ (g) is the initial weight (g) of the superabsorbent polymer, $W_3$ (g) is the sum of the weight of the superabsorbent polymer and the weight of the apparatus capable of providing a load for the superabsorbent polymer, and $W_4$ (g) is the sum of the weight of the superabsorbent polymer after allowing the superabsorbent polymer to absorb the physiological saline solution under a load (0.9 psi) for 1 hour and the weight of the apparatus capable of providing a load for the superabsorbent polymer.

The gel bed permeability (GBP) in the physiological saline solution may be measured in a unit of Darcy or $cm^2$ in accordance with the following method described in Patent Application No. 2014-7018005. 1 darcy means that a fluid of 1 cp viscosity flows 1 mm per sec through 1 $cm^2$ under a pressure gradient of 1 atm per 1 cm. The gel bed permeability has the same units as area, and 1 darcy is equal to $0.98692 \times 10^{-12}$ $m^2$ or $0.98692 \times 10^{-8}$ $cm^2$.

More specifically, GBP, as used herein, means a degree of penetration (or permeability) of a swollen gel layer (or bed) under what is commonly referred to as a free swell state of 0 psi (Gel Bed Permeability (GBP) Under 0 psi Swell Pressure Test), and may be measured by using an apparatus shown in FIGS. 1 to 3.

Referring to FIGS. 1 to 3, in an apparatus 500 for measuring GBP, a test apparatus assembly 528 includes a sample container 530 and a plunger 536. The plunger includes a shaft 538 having a cylinder hole bored down the longitudinal axis and a head 550 positioned at the bottom of the shaft. The shaft hole 562 has a diameter of about 16 mm. The plunger head is attached to the shaft, for example, by an adhesive. Twelve holes 544 are bored into the radial axis of the shaft, three positioned at every 90 degrees having diameters of about 6.4 mm. The shaft 538 is machined from a LEXAN rod or equivalent material and has an outer diameter of about 2.2 cm and an inner diameter of about 16 mm. The plunger head 550 has a concentric inner ring of seven holes 560 and an outer ring of 14 holes 554, all holes having a diameter of about 8.8 mm as well as a hole of about 16 mm aligned with the shaft. The plunger head 550 is machined from a LEXAN rod or equivalent material and has a height of about 16 mm and a diameter sized such that it fits within the cylinder 534 with minimum wall clearance but still slides freely. The total length of the plunger head 550 and shaft 538 is about 8.25 cm, but may be machined at the top of the shaft to obtain the desired mass of the plunger 536. The plunger 536 includes a 100 mesh stainless steel cloth screen 564 that is biaxially stretched to tautness and attached to the lower end of the plunger 536. The screen is attached to the plunger head 550 using an appropriate solvent that causes the screen to be securely adhered to the plunger head 550. Care must be taken to avoid excess solvent migrating into the open portions of the screen and reducing the open area for liquid flow. Acrylic solvent Weld-on 4 from IPS Corporation (having a place of business in Gardena, Calif., USA) may be suitably used. The sample container 530 includes a cylinder 534 and a 400 mesh stainless steel cloth screen 566 that is biaxially stretched to tautness and attached to the lower end of the cylinder 534. The screen is attached to the cylinder using an appropriate solvent that causes the screen to be securely adhered to the cylinder. Care must be taken to avoid excess solvent migrating into the open portions of the screen and reducing the open area for liquid flow. Acrylic solvent Weld-on 4 from IPS Corporation (having a place of business in Gardena, Calif., USA) may be suitably used. A gel particle sample (swollen superabsorbent polymer), indicated as 568 in FIG. 2, is supported on the screen 566 within the cylinder 534 during testing.

The cylinder 534 may be bored from a transparent LEXAN rod or equivalent material, or it may be cut from a LEXAN tubing or equivalent material, and has an inner diameter of about 6 cm (e.g., a cross-sectional area of about 28.27 $cm^2$), a wall thickness of about 0.5 cm and a height of about 7.95 cm. A step is machined into the outer diameter of the cylinder 534 such that a region 534a with an outer diameter of 66 mm exists for the bottom 31 mm of the cylinder 534. An o-ring 540 which fits the diameter of region 534a may be placed at the top of the step.

An annular weight 548 has a counter-bored hole about 2.2 cm in diameter and 1.3 cm deep so that it slips freely onto the shaft 538. The annular weight also has a thru-bore 548a of about 16 mm. The annular weight 548 may be made from stainless steel or from other suitable materials resistant to corrosion by 0.9% by weight of a physiological saline solution (sodium chloride aqueous solution). The combined weight of the plunger 536 and annular weight 548 equals about 596 g, which corresponds to a pressure applied to the sample 568 of about 0.3 psi, or about 20.7 dynes/cm² (2.07 kPa), over a sample area of about 28.27 cm².

When a test solution flows through the test apparatus during GBP testing, the sample container 530 generally rests on a weir 600. The purpose of the weir is to divert liquid that overflows the top of the sample container 530 and diverts the overflow liquid to a separate collection device 601. The weir may be positioned above a scale 602 with a beaker 603 resting on it to collect a physiological saline solution passing through the swollen sample 568.

To conduct the gel bed permeability test under "free swell" conditions, the plunger 536, with the weight 548 seated thereon, is placed in an empty sample container 530 and the height from the top of the weight 548 to the bottom of the sample container 530 is measured using a suitable gauge accurate to 0.01 mm. The force the thickness gauge applies during measurement should be as low as possible, preferably less than about 0.74 N. It is important to measure each empty sample container 530 and to keep track of which plunger 536 and weight 548 are used when using a multiple test apparatus.

Further, it is desirable that a base on which the sample container 530 is placed is level, and the top surface of the weight 548 is parallel to the bottom surface of the sample container. A test sample is prepared from a superabsorbent polymer to be tested for GBP. For example, a superabsorbent polymer having a particle size of about 300 μm to about 600 μm, which is prescreened through a US standard 30 mesh screen and retained on a US standard 50 mesh screen, is prepared as the test sample. About 2.0 g of the sample is placed in the sample container 530 and spread out evenly on the bottom of the sample container. The container, with 2.0 g of sample in it, without the plunger 536 and weight 548 therein, is then submerged in the 0.9% by weight of a physiological saline solution for about 60 minutes to allow the sample to swell free of any restraining load. At this time, the sample container 530 is set on a mesh located in a liquid reservoir so that the sample container 530 is raised slightly above the bottom of the liquid reservoir. The mesh does not inhibit the flow of the physiological saline solution into the sample container 530. A suitable mesh may be obtained as part number 7308 from Eagle Supply and Plastic (having a place of business in Appleton, Wis., USA). During saturation, a depth of the physiological saline solution may be controlled such that the surface within the sample container is defined solely by the sample, rather than the physiological saline solution.

At the end of this period, the plunger 536 and weight 548 assembly is placed on the saturated sample 568 in the sample container 530 and then the sample container 530, plunger 536, weight 548, and sample 568 are removed from the solution. Then, before GBP measurement, the sample container 530, plunger 536, weight 548, and sample 568 are to remain at rest for about 30 seconds on a large grid non-deformable plate of uniform thickness. The plate will prevent liquid in the sample container from being released onto a flat surface due to surface tension. The plate has an overall dimension of 7.6 cm×7.6 cm, and each grid has a size dimension of 1.59 cm long×1.59 cm wide×1.12 cm deep. A material suitable for the plate is a parabolic diffuser panel, catalogue number 1624K27, available from McMaster Carr Supply Company (having a place of business in Chicago, Ill., USA), which may then be cut to the proper dimensions.

The height from the top of the weight 548 to the bottom of the sample container 530 is measured again by using the same thickness gauge used previously, provided that the zero point is unchanged from the initial height measurement. The height measurement should be made as soon as practicable after the thickness gauge is engaged. The height measurement of the empty assembly where the plunger 536 and the weight 548 are placed in the empty sample container 530 is subtracted from the height measurement obtained after saturating the sample 568. The resulting value is the thickness or height "H" of the saturated sample 568. Further, if the plate is contained in the assembly containing the saturated sample 568, this plate must also be present when measuring the height of the empty assembly.

The GBP measurement is initiated by delivering a flow of 0.9% physiological saline solution into the sample container 530 with the saturated sample 568, plunger 536, and weight 548 inside. The flow rate of the physiological saline solution into the container is adjusted to cause the physiological saline solution to overflow the top of the cylinder 534, resulting in a consistent head pressure equal to the height of the sample container 530. The physiological saline solution may be added by any suitable means that is sufficient to ensure a small, but consistent amount of overflow from the top of the cylinder, such as with a metering pump 604. The overflow liquid is diverted into a separate collection device 601. The quantity of solution passing through the sample 568 versus time is measured gravimetrically using a scale 602 and a beaker 603. Data points from the scale 602 are collected every second for at least 60 seconds once the overflow has begun. Data collection may be taken manually or with data collection software. The flow rate, Q through the swollen sample 568 is determined in units of g/sec by a linear least-square fit of fluid (g) passing through the sample 568 versus time (sec).

GBP (cm²) may be calculated from the obtained data according to the following Calculation Formula 3 to confirm gel bed permeability:

$$K=[Q*H*\mu]/[A*\rho*P] \qquad \text{[Calculation Formula 3]}$$

wherein K is gel bed permeability (cm²),

Q is a flow rate (g/sec),

H is a height of swollen sample (cm),

μ is liquid viscosity (P) (about 1 cp for the test solution used in this test),

A is a cross-sectional area for liquid flow (28.27 cm² for the sample container used in this test), ρ is a liquid density (g/cm³) (about 1 g/cm³ for the test solution used in this test), and P is a hydrostatic pressure (dynes/cm²) (normally about 7,797 dynes/cm²).

The hydrostatic pressure is calculated from P=ρ*g*h, wherein ρ is a liquid density (g/cm³), g is gravitational acceleration (nominally 981 cm/sec²), and h is a fluid height (e.g., 7.95 cm for the GBP test described herein).

Lastly, absorbency under load (5 min gel-vac-AUL) of the superabsorbent polymer, which is measured by swelling the superabsorbent polymer in a physiological saline solution under a load of 0.3 psi for 5 minutes and removing residual liquid under vacuum, is a factor for evaluating absorption rate under load and performances, and may be measured as follows. First, the superabsorbent polymer is allowed to absorb the physiological saline solution under a load of about 0.3 psi for 5 minutes. Then, residual liquid not absorbed into the superabsorbent polymer is removed under vacuum. In this regard, residual liquid not absorbed between the superabsorbent polymer particles is removed, and liquid absorbed by the superabsorbent polymer is not removed under vacuum. Unlike a known method of measuring absorbency under load, a method of measuring 5 min gel-vac-AUL may evaluate absorbency under load of the superabsorbent polymer with more accuracy, because residual liquid existing between superabsorbent polymer particles does not influence the measurement values.

5 min gel-vac-AUL of the superabsorbent polymer may be calculated by the following Calculation Formula 4:

$$5 \text{ min } gel\text{-}vac\text{-}AUL(g/g) = [W_6(g) - W_5(g)]/W_0(g) \quad \text{[Calculation Formula 4]}$$

wherein $W_0$ (g) is an initial weight (g) of the superabsorbent polymer, $W_5$ (g) is the sum of the weight of the superabsorbent polymer and the weight of the apparatus capable of providing a load for the superabsorbent polymer, and $W_6$ (g) is the sum of the weight of the superabsorbent polymer which is measured after allowing the superabsorbent polymer to absorb the physiological saline solution under a load (0.3 psi) for 5 minutes and removing residual liquid using a vacuum apparatus, and the weight of the apparatus capable of providing a load for the superabsorbent polymer.

$W_0$ (g) described in Calculation Formulae 1, 2 and 4 corresponds to the initial weight before absorbing the physiological saline solution into the superabsorbent polymer, and may be the same as or different from each other.

Based on the above physical properties, it was confirmed that the preparation method of an embodiment may effectively prevent deterioration of physical properties after pulverization. In particular, the preparation method may minimize deterioration of liquid permeability, of which remarkable deterioration is inevitable due to pulverization of the superabsorbent polymer.

Accordingly, the superabsorbent polymer of another embodiment may exhibit minimized deterioration of physical properties after pulverization, thereby having not only excellent basic absorption performances but also excellent liquid permeability and absorption rate under no load or under load. As a result, the superabsorbent polymer may be applied to a variety of hygiene products such as diapers, etc., thereby exhibiting very excellent overall physical properties.

Hereinafter, the actions and effects of the present invention will be described in more detail with reference to specific Examples of the present invention. However, these Examples are for illustrative purposes only, and the scope of the invention is not intended to be limited thereby.

Example 1: Preparation of Superabsorbent Polymer 11 g (110 ppm with respect to a monomer composition) of 0.5% IRGACURE 819 initiator diluted with acrylic acid and 26 g of 5% polyethyleneglycol diacrylate (PEGDA, a molecular weight of 400) diluted with acrylic acid were mixed to prepare a solution (solution A).

5% trimethylolpropane triacrylate containing 9 mol % of ethylene oxide (Ethoxylated-TMPTA, TMP(EO)9TA, M-3190 Miwon Specialty Chemical Co., Ltd.) diluted with acrylic acid was used to prepare a solution (solution B).

Into a 2 L-volume glass reactor surrounded by a jacket in which a heating medium pre-cooled to 25° C. was circulated, 37 g of the solution A and 14 g of the solution B were injected. To the glass reactor, 800 g of a 24% caustic soda solution (solution C) was slowly added dropwise and mixed. After confirming that the temperature of the mixed solution increased to about 72° C. or higher by neutralization heat upon adding dropwise the solution C, the mixed solution was left until it was cooled. A neutralization degree of acrylic acid in the mixed solution thus obtained was about 70 mol %.

Subsequently, the above-prepared mixed solution was poured in a Vat-type tray (15 cm in width×15 cm in length) installed in a square polymerizer which had a light irradiation device installed at the top and was preheated to 80° C., and the mixed solution was subjected to light irradiation. It was confirmed that at about 20 seconds after light irradiation, gel was generated from the surface, and at about 30 seconds after light irradiation, polymerization occurred. Then, the reaction was allowed for additional 2 minutes, and the polymerized sheet was taken and cut in a size of 3 cm×3 cm, and then subjected to a chopping process using a meat chopper to prepare the cut sheet as crumbs.

Subsequently, the crumbs were dried in an oven capable of shifting airflow up and down. The crumbs were uniformly dried by flowing hot air at 180° C. from the bottom to the top for 15 minutes and from the top to the bottom for 15 minutes such that the dried crumbs had a water content of about 2% or less. The dried crumbs were pulverized using a pulverizer and sorted by size, and a base polymer having a size of about 150 μm to about 850 μm was obtained.

Thereafter, 100 g of the base polymer was mixed with a crosslinking agent solution which was prepared by mixing 3 g of water, 3.5 g of methanol, 0.4 g of ethylene carbonate, 0.05 g of polyvinyl alcohol (weight average molecular weight: 80,000 g/mol, degree of hydration: 88%), and 0.05 g of Aerosil 380 (EVONIK), and then surface crosslinking reaction was allowed at 190° C. for 30 minutes. The resulting product was used to evaluate physical properties of the superabsorbent polymer before pulverization.

Meanwhile, the resulting product was pulverized by using a ball mill under conditions of 300 rpm and 20 minutes. The pulverized superabsorbent polymer was size-sorted through a US standard 30 mesh screen and a US standard 50 mesh screen to obtain the pulverized superabsorbent polymer having a particle size of about 300 μm to about 600 μm, which was used to evaluate physical properties of the superabsorbent polymer after pulverization.

Example 2: Preparation of Superabsorbent Polymer

Superabsorbent polymers before and after pulverization were obtained in the same manner as in Example 1, except that 0.1 g of polyvinyl alcohol (weight average molecular weight: 80,000 g/mol, degree of hydration: 88%) was used and Aerosil 380 was not used in Example 1.

Example 3: Preparation of Superabsorbent Polymer

Superabsorbent polymers before and after pulverization were obtained in the same manner as in Example 1, except that 0.05 g of Arabic gum (weight average molecular weight: 600,000 g/mol) was used instead of polyvinyl alcohol (weight average molecular weight: 80,000 g/mol, degree of hydration: 88%) in Example 1.

Example 4: Preparation of Superabsorbent Polymer

Superabsorbent polymers before and after pulverization were obtained in the same manner as in Example 1, except that 0.1 g of polyethylene glycol (weight average molecular weight: 8,000 g/mol) was used instead of 0.05 g of polyvinyl alcohol (weight average molecular weight: 80,000 g/mol, degree of hydration: 88%) and Aerosil 380 was not used in Example 1.

Comparative Example 1: Preparation of Superabsorbent Polymer

Superabsorbent polymers before and after pulverization were obtained in the same manner as in Example 1, except that 0.1 g of Aerosil 380 was used and polyvinyl alcohol was not used in Example 1.

Comparative Example 2: Preparation of Superabsorbent Polymer

Superabsorbent polymers before and after pulverization were obtained in the same manner as in Example 1, except that 0.1 g of Aerosil 200 (EVONIK) was used instead of 0.05 g of Aerosil 380 and polyvinyl alcohol was not used in Example 1.

Experimental Example: Evaluation of Superabsorbent Polymer

Properties of the superabsorbent polymers before and after pulverization which were prepared in Examples 1 to 4 and Comparative Examples 1 to 2 were evaluated as follows, and shown in the following Tables 1 and 2.

(1) Centrifuge Retention Capacity (CRC)

Centrifuge retention capacity (CRC) in a physiological saline solution was measured for the superabsorbent polymers before pulverization and after pulverization which were prepared in Examples 1 to 4 and Comparative Examples 1 to 2 in accordance with EDANA method WSP 241.2.

In detail, among the superabsorbent polymers to be tested for centrifuge retention capacity, superabsorbent polymers having a particle size of 300 μm to 600 μm, which were passed through a US standard 30 mesh screen and retained on a US standard 50 mesh screen, were prepared.

The superabsorbent polymer $W_0$ (g, about 0.2 g) having a particle size of 300 μm to 600 μm was uniformly placed into a nonwoven-fabric-made bag, followed by sealing. Then, the bag was immersed into 0.9% by weight of a physiological saline solution at room temperature. 30 minutes later, the bag was drained at 250 G for 3 minutes with a centrifuge, and the weight $W_2$ (g) of the bag was then measured. Meanwhile, the same procedure was carried out using an empty bag having no superabsorbent polymer, and the resultant weight $W_1$ (g) was measured.

Each of the weights thus obtained was used to confirm centrifuge retention capacity according to the following Equation 1:

$$CRC(g/g) = \{[W_2(g) - W_1(g)]/W_0(g)\} - 1 \quad \text{[Calculation Formula 1]}$$

wherein $W_0$ (g) is an initial weight (g) of the superabsorbent polymer having a particle size of 300 μm to 600 μm, $W_1$ (g) is a weight of an apparatus which is measured after draining water off at 250 G for 3 minutes with a centrifuge without using the superabsorbent polymer, and $W_2$ (g) is the weight of the apparatus including the superabsorbent polymer, which is measured after immersing the superabsorbent polymer in 0.9% by weight of the physiological saline solution at room temperature for 30 minutes and draining water off at 250 G for 3 minutes with a centrifuge.

(2) Absorbency Under Load (AUL)

Absorbency under load (AUL) of 0.9 psi in the physiological saline solution was measured for the superabsorbent polymers before and after pulverization prepared in Examples 1 to 4 and Comparative Examples 1 to 2 according to EDANA method WSP 242.2.

In detail, a 400 mesh stainless steel net was installed in the bottom of a plastic cylinder having an internal diameter of 25 mm. The superabsorbent polymer $W_0$ (g, 0.16 g) to be tested for absorbency under load was uniformly scattered on the screen at room temperature and humidity of 50%. Subsequently, a piston which may uniformly provide a load of 6.3 kPa (0.9 psi) was put thereon, in which an external diameter of the piston was slightly smaller than 25 mm, there was no gab between the internal wall of the cylinder and the piston, and the jig-jog of the cylinder was not interrupted. At this time, the weight $W_3$ (g) of the apparatus was measured.

After putting a glass filter having a diameter of 90 mm and a thickness of 5 mm in a petri dish having a diameter of 150 mm, a physiological saline solution of 0.9% by weight was poured in the dish until the surface level of the physiological saline solution became equal to the upper surface of the glass filter. A sheet of filter paper having a diameter of 90 mm was put on the glass filter.

Subsequently, the prepared apparatus was put on the filter paper and the superabsorbent polymer in the apparatus was allowed to swell by the physiological solution under a load. After 1 hr, the weight $W_4$ (g) of the apparatus containing the swollen superabsorbent polymer was measured.

The weights thus obtained were used to calculate absorbency under load according to the following Equation 2:

$$AUL(g/g) = [W_4(g) - W_3(g)]/W_0(g) \quad \text{[Calculation Formula 2]}$$

wherein $W_0$ (g) is an initial weight (g) of the superabsorbent polymer, $W_3$ (g) is the sum of the weight of the superabsorbent polymer and the weight of the apparatus capable of providing a load for the superabsorbent polymer, and $W_4$ (g) is the sum of the weight of the superabsorbent polymer after allowing the superabsorbent polymer to absorb the physiological saline solution under a load (0.9 psi) for 1 hour, and the weight of the apparatus capable of providing the load for the superabsorbent polymer.

(3) Gel Bed Permeability (GBP)

Free swell gel bed permeability (GBP) in a physiological saline solution was measured for the superabsorbent polymers before and after pulverization which were prepared in Examples 1 to 4 and Comparative Examples 1 to 2 according to the following method described in Patent Application. No. 2014-7018005.

In detail, an apparatus illustrated in FIGS. 1 to 3 was used to conduct a free swell GBP test. First, a plunger 536, with a weight 548 seated thereon, was placed in an empty sample container 530 and the height from the top of the weight 548 to the bottom of the sample container 530 was measured using a suitable gauge accurate to 0.01 mm. The force the thickness gauge applies during measurement was controlled to less than about 0.74 N.

Meanwhile, among the superabsorbent polymers to be tested for GBP, superabsorbent polymers, which were passed through a US standard 30 mesh screen and retained on a US standard 50 mesh screen, were selected to obtain the superabsorbent polymer having a particle size of 300 μm to 600 μm.

About 2.0 g of the size-sorted superabsorbent polymer was placed in a sample container 530 and spread out evenly on the bottom of the sample container. This container without the plunger 536 and weight 548 therein was then submerged in the 0.9% by weight of a physiological saline solution for about 60 minutes to allow the superabsorbent polymer to swell free of any restraining load. At this time, the sample container 530 was set on a mesh located in a liquid reservoir so that the sample container 530 was raised slightly above the bottom of the liquid reservoir. The mesh did not inhibit the flow of the physiological saline solution into the sample container 530. During saturation, a depth of the physiological saline solution was controlled such that the surface within the sample container was defined solely by the swollen superabsorbent polymer, rather than the physiological saline solution.

At the end of this period, the plunger 536 and weight 548 assembly was placed on the swollen superabsorbent polymer 568 in the sample container 530 and then the sample container 530, plunger 536, weight 548, and swollen superabsorbent polymer 568 were removed from the solution. Then, before GBP measurement, the sample container 530, plunger 536, weight 548, and swollen superabsorbent polymer 568 were to remain at rest for about 30 seconds on a large grid non-deformable plate of uniform thickness. The height from the bottom of the weight 548 to the top of the sample container 530 was measured again by using the same thickness gauge used previously. The height measurement of the apparatus where the plunger 536 and the weight 548 were placed in the empty sample container 530 was subtracted from the height measurement of the apparatus containing the swollen superabsorbent polymer 568 to obtain the thickness or height "H" of the swollen superabsorbent polymer.

For GBP measurement, a flow of 0.9% physiological saline solution was delivered into the sample container 530 with the swollen superabsorbent polymer 568, plunger 536, and weight 548 inside. The flow rate of the physiological saline solution into the container 530 was adjusted to cause the physiological saline solution to overflow the top of the cylinder 534, resulting in a consistent head pressure equal to the height of the sample container 530. The quantity of solution passing through the swollen superabsorbent polymer 568 versus time was measured gravimetrically using a scale 602 and a beaker 603. Data points from the scale 602 were collected every second for at least 60 seconds once the overflow has begun. The flow rate, Q through the swollen superabsorbent polymer 568 was determined in units of g/sec by a linear least-square fit of fluid (g) passing through the swollen superabsorbent polymer 568 versus time (sec).

GBP (cm$^2$) was calculated from the obtained data according to the following Calculation Formula 3:

$$K=[Q*H*\mu]/[A*\rho*P]$$ [Calculation Formula 3]

wherein K is gel bed permeability (cm$^2$),
Q is a flow rate (g/sec),
H is a height of swollen superabsorbent polymer (cm),
$\mu$ is liquid viscosity (P) (about 1 cp for the physiological saline solution used in this test),
A is a cross-sectional area for liquid flow (28.27 cm$^2$ for the sample container used in this test),
$\rho$ is a liquid density (g/cm$^3$) (about 1 g/cm$^3$ for the physiological solution used in this test), and P is a hydrostatic pressure (dynes/cm$^2$) (normally about 7,797 dynes/cm$^2$).

The hydrostatic pressure is calculated from $P=\rho*g*h$, wherein $\rho$ is a liquid density (g/cm$^3$), g is gravitational acceleration (nominally 981 cm/sec$^2$), and h is a fluid height (e.g., 7.95 cm for the GBP test described herein).

At least two samples were tested, and an average of the results was determined as free swell GBP of the superabsorbent polymer, and the unit was converted to darcy (1 darcy=0.98692×10$^{-8}$ cm$^2$) and shown in Table 2.

(4) 5 min gel-vac-AUL 5 min gel-vac-AUL was measured for the superabsorbent polymers before and after pulverization prepared in Examples 1 to 4 and Comparative Examples 1 to 2 according to the following method.

In detail, a 400 mesh stainless steel net was installed in the bottom of a plastic cylinder having an internal diameter of 25 mm. The superabsorbent polymer $W_0$ to be tested for 5 min gel-vac-AUL was uniformly scattered on the screen at room temperature and humidity of 50%. Subsequently, a piston which may uniformly provide a load of 0.3 psi was put thereon, in which an external diameter of the piston was slightly smaller than 25 mm, there was no gab between the internal wall of the cylinder and the piston, and the jig-jog of the cylinder was not interrupted. At this time, the weight $W_5$ (g) of the apparatus was measured.

After putting a glass filter having a diameter of 90 mm and a thickness of 5 mm in a petri dish having a diameter of 150 mm, a physiological saline solution of 0.9% by weight was poured in the dish until the surface level of the physiological saline solution became equal to the upper surface of the glass filter. A sheet of filter paper having a diameter of 90 mm was put on the glass filter.

Subsequently, the prepared apparatus was put on the filter paper and the superabsorbent polymer in the apparatus was allowed to swell by the physiological solution under a load. 5 minutes later, residual liquid was removed by using a vacuum pump. At this time, residual liquid not absorbed between the superabsorbent polymer particles was removed. Then, the weight $W_6$ (g) of the apparatus including the superabsorbent polymer was measured.

5 min gel-vac-AUL was calculated using the measured weight according to the following Calculation Formula 4:

$$5 \min gel\text{-}vac\text{-}AUL(g/g)=[W_6(g)-W_5(g)]/W_0(g)$$ [Calculation Formula 4]

wherein $W_0$ (g) is an initial weight (g) of the superabsorbent polymer, $W_5$ (g) is the sum of the weight of the superabsorbent polymer and the weight of the apparatus capable of providing a load for the superabsorbent polymer, and $W_6$ (g) is the sum of the weight of the superabsorbent polymer which is measured after allowing the superabsorbent polymer to absorb the physiological saline solution under a load (0.3 psi) for 5 minutes and removing residual liquid between the swollen superabsorbent polymer particles using a vacuum pump, and the weight of the apparatus capable of providing a load for the superabsorbent polymer.

TABLE 1

|  | CRC [g/g] | | | 0.9 AUL [g/g] | | |
| --- | --- | --- | --- | --- | --- | --- |
|  | Before pulverization | After pulverization | Increase/decrease rate [%] | Before pulverization | After pulverization | Increase/decrease rate [%] |
| Example 1 | 30.4 | 31.4 | 3.2 | 22.3 | 20.8 | −7.2 |
| Example 2 | 29.8 | 31.1 | 4.2 | 22.8 | 21.4 | −6.5 |
| Example 3 | 29.4 | 31.0 | 5.2 | 22.0 | 21.1 | −4.3 |

TABLE 1-continued

|  | CRC [g/g] | | | 0.9 AUL [g/g] | | |
| --- | --- | --- | --- | --- | --- | --- |
|  | Before pulverization | After pulverization | Increase/ decrease rate [%] | Before pulverization | After pulverization | Increase/ decrease rate [%] |
| Example 4 | 30.7 | 31.5 | 2.5 | 22.0 | 20.9 | −5.3 |
| Comparative Example 1 | 30.4 | 31.0 | 1.9 | 21.1 | 19.9 | −6.0 |
| Comparative Example 2 | 30.0 | 30.9 | 2.9 | 21.0 | 19.5 | −7.7 |

TABLE 2

|  | GBP [darcy] | | | 5 min gel-vac AUL [g/g] | | |
| --- | --- | --- | --- | --- | --- | --- |
|  | Before pulverization | After pulverization | Increase/ decrease rate [%] | Before pulverization | After pulverization | Increase/ decrease rate [%] |
| Example 1 | 30.5 | 17.3 | −43.3 | 18.5 | 18.0 | −2.8 |
| Example 2 | 27.5 | 15.2 | −44.7 | 18.6 | 18.3 | −1.6 |
| Example 3 | 34.0 | 16.0 | −52.9 | 18.5 | 18.0 | −2.8 |
| Example 4 | 30.0 | 14.5 | −51.7 | 18.5 | 18.2 | −1.6 |
| Comparative Example 1 | 38.0 | 9.0 | −76.3 | 17.5 | 16.5 | −6.1 |
| Comparative Example 2 | 36.0 | 10.0 | −72.2 | 18.0 | 17.2 | −4.7 |

The increase/decrease rate in Tables 1 and 2 was calculated by dividing a value, which was obtained by subtracting the value measured before pulverization from the value measured after pulverization, by the value measured before pulverization, and then multiplying the resulting value by 100.

Referring to Tables 1 and 2, it was confirmed that the superabsorbent polymer according to an embodiment of the present invention exhibits not only excellent absorption performances but also remarkable reduction in the deterioration of physical properties after pulverization, as compared to the known superabsorbent polymer.

REFERENCE NUMERALS

- 500: GBP measuring apparatus
- 528: Test apparatus assembly
- 530: Sample container
- 534: Cylinder
- 534a: Region with outer diameter of 66 mm
- 536: Plunger
- 538: Shaft
- 540: O-ring
- 544, 554, 560: Holes
- 548: Annular weight
- 548a: Thru-bore
- 550: Plunger head
- 562: Shaft hole
- 564: Stainless steel cloth screen of 100 mesh
- 566: Stainless steel cloth screen of 400 mesh
- 568: Sample
- 600: Weir
- 601: Collection device
- 602: Scale
- 603: Beaker
- 604: Metering pump

The invention claimed is:

1. A superabsorbent polymer comprising a base polymer powder including a crosslinking polymer of water-soluble ethylene-based unsaturated monomers having acidic groups which are at least partially neutralized; and a surface-crosslinked layer formed on the base polymer powder, wherein the surface-crosslinked layer is obtained by reacting the base polymer powder with a surface crosslinking agent solution comprising a polyvinyl alcohol thickener having a weight average molecular weight of 300 g/mol to 1,000,000 g/mol, an inorganic material, and a surface crosslinking agent, and the polyvinyl alcohol thickener is included in an amount of 0.01 to 1 part by weight with respect to 100 parts by weight of the base polymer powder, and wherein the superabsorbent polymer has a GBP reduction rate of the following Equation 1 of −55% to 0%:

$$GBP \text{ reduction rate } (\%) = \{(G_1 - G_0)/G_0\} * 100 \quad \text{[Equation 1]}$$

wherein $G_0$ is an initial gel bed permeability of the superabsorbent polymer, and $G_1$ is a gel bed permeability of a superabsorbent polymer having a particle size of 300 μm to 600 μm, which is obtained by pulverizing the superabsorbent polymer using a ball mill under 300 rpm for 20 minutes and then size-sorting the pulverized superabsorbent polymer.

2. The superabsorbent polymer of claim 1, which has a reduction rate of absorbency under load of the following Equation 2 of −4% to 0%:

$$\text{Reduction rate of absorbency under load } (\%) = \{(A_1 - A_0)/A_0\} * 100 \quad \text{[Equation 2]}$$

wherein $A_0$ is an initial absorbency under load of the superabsorbent polymer, on which the surface-crosslinked layer is formed, as calculated by the following Calculation Formula 4, and $A_1$ is an absorbency under load of the superabsorbent polymer having a particle size of 300 μm to 600 μm, which is obtained by pulverizing the superabsorbent polymer using a ball mill under 300 rpm for 20 minutes and then size-sorting the pulverized superabsorbent polymer, as calculated by the following Calculation Formula 4, $$5 \text{ min } gel\text{-}vac\text{-}AUL(g/g) = [W_6(g) - W_5(g)]/W_0(g) \quad \text{[Calculation Formula 4]}$$

wherein $W_0(g)$ is an initial weight (g) of the superabsorbent polymer, $W_5(g)$ is the sum of the weight of the superabsorbent polymer and a weight of an apparatus capable of providing a load for the superabsorbent polymer, and $W_6(g)$ is the sum of the weight of the superabsorbent polymer, which is measured after allowing the superabsorbent polymer to absorb a physiological saline solution under a load (0.3 psi) for 5 minutes and removing residual liquid using a vacuum apparatus, and the weight of the apparatus capable of providing a load for the superabsorbent polymer.

3. The superabsorbent polymer of claim 1, wherein with regard to the superabsorbent polymer having a particle size of 300 μm to 600 μm, which is obtained by pulverizing the superabsorbent polymer using a ball mill under 300 rpm for 20 minutes and then size-sorting the pulverized superabsorbent polymer, centrifuge retention capacity (CRC) in a physiological saline solution is 30 g/g to 32 g/g, absorbency under load (AUL) of 0.9 psi in the physiological saline solution is 20 to 22 g/g, free swell gel bed permeability (GBP) in the physiological saline solution is 12 darcy to 100 darcy, and absorbency under load (5 min gel-vac-AUL) of the superabsorbent polymer, as measured after swelling the superabsorbent polymer in the physiological saline solution under a load of 0.3 psi for 5 minutes and removing residual liquid under vacuum, is 17 g/g to 19 g/g.

4. The superabsorbent polymer of claim 1, wherein the inorganic material is included in an amount of more than 0 part by weight to 0.07 parts by weight with respect to 100 parts by weight of the base polymer powder.

5. The superabsorbent polymer of claim 1, wherein the surface crosslinking agent is one or more polyols selected from the group consisting of ethylene glycol, propylene glycol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol, and glycerol; or one or more carbonate-based compounds selected from the group consisting of ethylene carbonate and propylene carbonate.

6. The superabsorbent polymer of claim 1, wherein the surface crosslinking agent is included in an amount of 0.01 to 4 parts by weight with respect to 100 parts by weight of the base polymer powder.

* * * * *